US00PP27802P2

(12) United States Plant Patent
Flore

(10) Patent No.: US PP27,802 P2
(45) Date of Patent: Mar. 21, 2017

(54) ***PHALAENOPSIS* PLANT NAMED 'MI00178'**

(50) Latin Name: *Phalaenopsis hybrida*
Varietal Denomination: MI00178

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 14/756,930

(22) Filed: Oct. 30, 2015

(51) Int. Cl.
*A01H 5/02* (2006.01)

(52) U.S. Cl.
USPC ..... Plt./311

(58) Field of Classification Search
USPC ..... Plt./311
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phalaenopsis* plant named 'MI00178', characterized by its upright plant habit; moderately vigorous growth habit; strong flowering stems; freely flowering habit; typically two panicles or racemes per plant; each inflorescence with numerous flowers; showy light violet-colored flowers that are densely covered with red purple and dark purple-colored spots and marbling; and ease of production.

2 Drawing Sheets

Botanical designation: *Phalaenopsis hybrida.*
Cultivar denomination: 'MI00178'.

BACKGROUND OF THE INVENTION

The present invention relates to a new and distinct cultivar of *Phalaenopsis* plant, botanically known as *Phalaenopsis hybrida*, and hereinafter referred to by the name 'MI00178'.

The new *Phalaenopsis* plant is a product of a planned breeding program conducted by the Inventor in Lochristi, Belgium. The objective of the breeding program is to develop new freely flowering *Phalaenopsis* plants with unique and attractive flower patterns and coloration.

The new *Phalaenopsis* plant originated from a cross-pollination in September, 2005 in Lochristi, Belgium of a proprietary selection of *Phalaenopsis hybrida* identified as code number PHM00008, not patented, as the female, or seed, parent with a proprietary selection of *Phalaenopsis hybrida* identified as code number PHM00045, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in June, 2008.

Asexual reproduction of the new *Phalaenopsis* plant by in vitro propagation (tissue culture) in a controlled environment in Lochristi, Belgium since February, 2010 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00178'. These characteristics in combination distinguish 'MI00178' as a new and distinct *Phalaenopsis* plant:

1. Upright plant habit.
2. Moderately vigorous growth habit.
3. Strong flowering stems.
4. Freely flowering habit; typically two panicles or racemes per plant; each inflorescence with numerous flowers.
5. Showy light violet-colored flowers that are densely covered with red purple and dark purple-colored spots and marbling.
6. Ease of production.

Plants of the new *Phalaenopsis* can be compared to plants of the female parent selection. Plants of the new *Phalaenopsis* differ primarily from plants of the female parent selection in flower color as plants of the female parent selection have dark purple-colored petals and sepals without spots and marbling. Additionally, the callosities of flowers of the new *Phalaenopsis* plant are grey purple in color whereas the callosities of flowers of the female parent selection are yellow in color with fine purple-colored dots.

Plants of the new *Phalaenopsis* can be compared to plants of the male parent selection. Plants of the new *Phalaenopsis* differ primarily from plants of the male parent selection in flower color as plants of the male parent selection have white-colored petals and sepals with red purple-colored marbling. Additionally, plants of the new *Phalaenopsis* are more freely flowering than plants of the male parent selection.

Plants of the new *Phalaenopsis* can be compared to plants of *Phalaenopsis hybrida* 'CX377', not patented. In side-by-side comparisons conducted in Lochristi, Belgium, plants of the new *Phalaenopsis* differ primarily from plants of 'CX377' in flowering habit as plants of the new *Phalaenopsis* typically produce two inflorescences each with numerous flowers whereas plants of 'CX377' typically produce one inflorescence with few flowers.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00178' grown in a container.

The photograph on the second sheet is a close-up view of typical flowers of 'MI00178'.

DETAILED BOTANICAL DESCRIPTION

The aforementioned photographs and following observations and measurements describe plants grown during the summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were exposed to eight weeks of cooling to induce flowering. Plants were 76 weeks from propagation when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00178'.

Parentage:

- *Female parent*.—Proprietary selection of *Phalaenopsis hybrida* identified as code number PHM00008, not patented.
- *Male parent*.—Proprietary selection of *Phalaenopsis hybrida* identified as code number PHM00045, not patented.

Propagation:

- *Type*.—By in vitro propagation (tissue culture).
- *Time to initiate roots, summer*.—About nine to ten weeks at temperatures about 26° C.
- *Time to initiate roots, winter*.—About ten to eleven weeks at temperatures about 26° C.
- *Time to produce a rooted young plant, summer*.—About 140 to 160 weeks at temperatures about 26° C.
- *Time to produce a rooted young plant, winter*.—About 150 to 180 weeks at temperatures about 26° C.
- *Root description*.—Thick, fleshy; typically grey green in color, towards the apex, close to light green occasionally with a purple-colored blush.
- *Rooting habit*.—Non-branching; sparse.

Plant description:

- *Plant form and growth habit*.—Herbaceous epiphyte; upright plant habit with typically two panicles or racemes per plant, each inflorescence with numerous flowers; monopodial; moderately vigorous growth habit and moderate growth rate; easy to produce.
- *Plant height, substrate level to top of foliar plane*.—About 11.4 cm.
- *Plant height, substrate level to top of inflorescences*.—About 58.8 cm.
- *Plant diameter or spread*.—About 36 cm.

Leaf description:

- *Arrangement*.—Distichous, simple; sessile.
- *Length*.—About 25.7 cm.
- *Width*.—About 7.2 cm.
- *Aspect*.—Arching.
- *Shape*.—Narrowly oblong to narrowly obovate.
- *Apex*.—Acute, unequal.
- *Base*.—Sheathing.
- *Margin*.—Entire; slightly revolute.
- *Texture, upper and lower surfaces*.—Slightly furrowed; glabrous; durable.
- *Luster, upper and lower surfaces*.—Moderately glossy.
- *Venation pattern*.—Camptodromous.
- *Color*.—Developing and fully expanded leaves, upper surface: Close to between N137A and 147A; venation, close to between N137A and 147A. Developing and fully expanded leaves, lower surface: Close to 146A to 146B; venation, close to 144A.

Inflorescence description:

- *Appearance and flowering habit*.—Showy zygomorphic flowers arranged on axillary panicles or racemes; typically two panicles or racemes per plant; each inflorescence with about 15 flowers; flowers face outwardly on arching inflorescences supported by strong upright peduncles; flowers with three petals, one petal transformed into a labellum and three sepals.
- *Fragrance*.—None detected.
- *Time to flower*.—Plants begin flowering about 18 weeks after an inductive cooling period.
- *Flower longevity*.—Individual flowers maintain good substance for about three months on the plant; flowers not persistent.
- *Inflorescence length* (*lowermost flower to inflorescence apex*).—About 29 cm.
- *Inflorescence width*.—About 18.1 cm to 28 cm.
- *Flower buds*.—Height: About 8 mm. Diameter: About 8 mm. Shape: Ovoid. Color: Close to N200A tinged with close to 152A.
- *Flower diameter*.—About 9.2 cm.
- *Flower depth*.—About 3.3 cm.
- *Petals, quantity and arrangement*.—Three, two lateral petals and one lower petal transformed into a labellum.
- *Lateral petals*.—Length: About 4.5 cm. Width: About 5.4 cm. Shape: Reniform. Apex: Rounded. Margin: Entire. Texture, upper and lower surfaces: Glabrous; velvety. Luster, upper and lower surfaces: Matte. Color: When opening, upper surface: Close to 84C to 84D; tinged (especially towards the margins) with close to 77B; densely spotted and marbled with close to 59A and N79C. When opening, lower surface: Close to 76B; venation, close to 77D. Fully opened, upper surface: Close to 84C to 84D; tinged towards the margins with close to 77C; densely spotted and marbled with close to 59A, 71A and N79C; color does not fade with development. Fully opened, lower surface: Close to 84D; spots and marbling visible from upper surface visible, close to 85C; color does not fade with development.
- *Labellum*.—Length: About 2.8 cm. Width: About 2.4 cm. Shape: Tri-lobed; two lateral lobes, reniform;

central lobe, hastate. Apex: Lateral lobes, rounded; central lobe, cleft with two long narrow recurved tips. Callosities: Located at the base of the labellum and attachment point of the lateral petals; about 4 mm in length, about 6 mm in width and about 6 mm in height. Margin: Entire. Texture, upper and lower surfaces: Glabrous; moderately velvety. Luster, upper and lower surfaces: Matte. Color: When opening, upper surface: Lateral lobes: Close to 59B; towards the apex, tinged with close to 72A; towards the base, close to 11C and 11D and heavily marbled with close to between 59A and 187A. Central lobe: Close to between 59B to 60A; main vein, close to N186C. Callosities: Close to 187A; towards the edges, close to 10B to 10D. When opening, lower surface: Lateral lobes: Close to 59B; towards the apex, tinged with close to 72B; towards the base, close to between 76D and N155A and slightly tinged with close to 10A to 10B. Central lobe: Close to 72B; tips and margins, close to 59B. Fully opened, upper surface: Lateral lobes: Close to 59B; towards the apex, tinged with close to 72A; towards the base, close to 11C and 11D and heavily marbled with close to between 59A and 187A. Central lobe: Close to between 59B to 60A; main vein, close to N186C. Callosities: Close to 187A; towards the edges, close to 10A. Fully opened, lower surface: Lateral lobes: Close to 59B; towards the apex, tinged with close to 72B; towards the base, close to between 76D and N155A and slightly tinged with close to 10A to 10B. Central lobe: Close to 72B; tips and margins, close to 59A to 59B; small central spot, close to between 84D to 85D.

*Sepals, quantity and arrangement*.—Three, two lower lateral sepals and one upper dorsal sepal.

*Lateral sepals*.—Length: About 4.9 cm. Width: About 3.1 cm. Shape: Ovate. Apex: Broadly acute. Base: Obtuse to truncate. Margin: Entire. Texture, upper and lower surfaces: Glabrous; velvety. Luster, upper and lower surfaces: Matte. Color: When opening, upper surface: Close to 84C; towards the apex tinged with close to 75B; towards the base, close to 150D; densely spotted and marbled with close to 59A, 59B and N79C. When opening, lower surface: Close to 76B to 76C; towards the base, strongly tinged with close to 161B to 161C; venation, close to N78C to N78D. Fully opened, upper surface: Close to 84C; towards the apex tinged with close to 75B; towards the base slightly tinged with close to 150D; densely spotted and marbled with close to 59A, 59B and N79C. Fully opened, lower surface: Close to 76B to 76C; towards the base, slightly tinged with close to 153D; main vein tinged with close to N78B.

*Dorsal sepal*.—Length: About 4.7 cm. Width: About 3.7 cm. Shape: Ovate to broadly elliptic. Apex: Obtuse. Base: Obtuse to truncate. Margin: Entire. Texture, upper and lower surfaces: Glabrous; velvety. Luster, upper and lower surfaces: Matte. Color: When opening, upper surface: Close to between 84D and N155B; towards the apex and base, tinged with close to N74C; densely spotted and marbled with close to 59B and N79C. When opening, lower surface: Close to 76B to 76C; towards the apex, close to N78C to N78D; venation, close to N78C to N78D. Fully opened, upper surface: Close to between N155A and NN155D; densely spotted and marbled with close to 71A and N79C. Fully opened, lower surface: Close to 76D tinged with close to 77D.

*Peduncles*.—Length: About 64.9 cm. Diameter: About 5.5 mm. Strength: Strong. Aspect: Upright to about 45° from vertical. Texture: Smooth, glabrous. Luster: Matte. Color: Close to between N200A and 203A heavily spotted with close to 146A.

*Pedicels*.—Length: About 4.9 cm. Diameter: About 3 mm. Strength: Moderately strong. Aspect: About 70° from peduncle axis. Texture: Smooth, glabrous. Luster: Matte. Color: Close to 146C to 146D; proximally, close to 146B; distally, close to 77D.

*Reproductive organs*.—Androecium: Column length: About 8.5 mm. Column width: About 6 mm. Column color: Close to N78A. Pollinia quantity: Two. Pollinia diameter (per two pollinia): About 2.5 mm. Pollinia color: Close to 21A. Gynoecium: Stigma length: About 4 mm. Stigma width: About 5 mm. Stigma shape: Reniform to nearly orbicular. Stigma color: Close to N155A. Ovary length: About 4 mm. Ovary diameter: About 3 mm. Ovary color: Close to 146C to 146D; towards the apex, close to 77D. Seeds and fruits: Seed and fruit development have not been observed on plants of the new *Phalaenopsis*.

Disease & pest resistance: Plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00178' as illustrated and described.

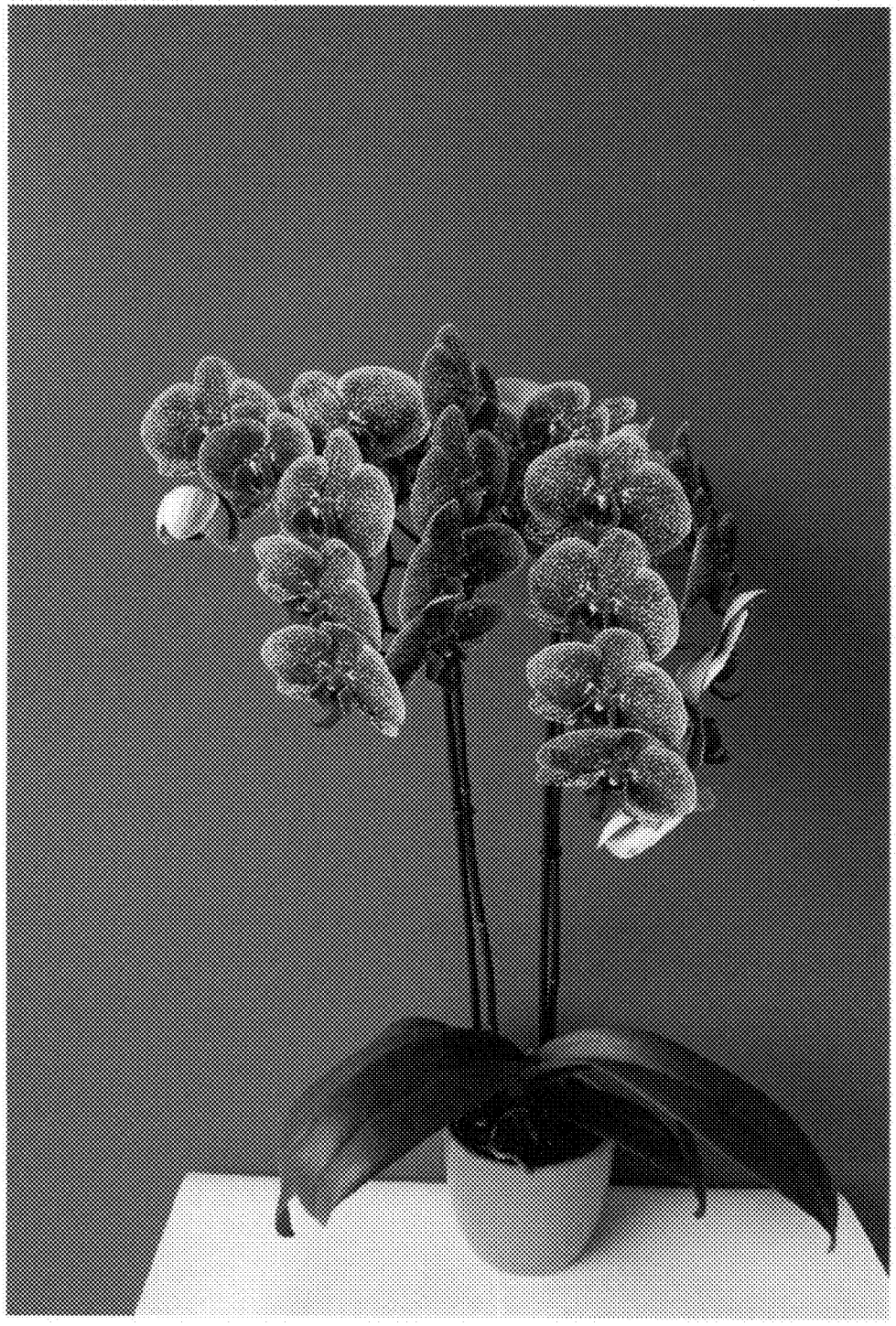

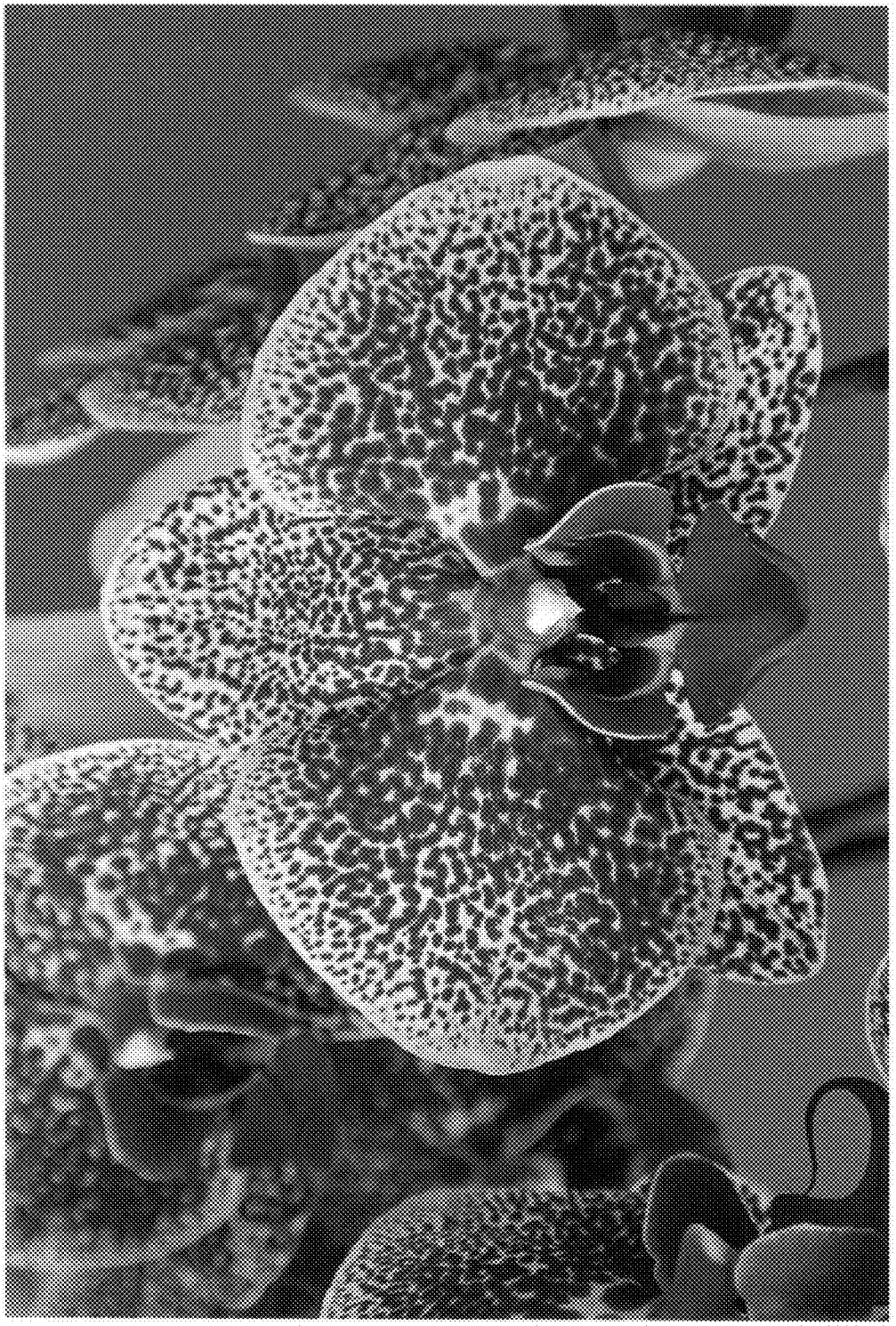

* * * * *